(12) United States Patent
Lee et al.

(10) Patent No.: US 9,523,689 B2
(45) Date of Patent: Dec. 20, 2016

(54) TREATING BLADDER CANCER PATIENTS AND IDENTIFYING BLADDER CANCER PATIENTS RESPONSIVE TO TREATMENT

(71) Applicant: Mayo Foundation for Medical Education and Research, Rochester, MN (US)

(72) Inventors: Nancy A. Lee, Scottsdale, AZ (US); James J. Lee, Scottsdale, AZ (US); Erik P. Castle, Scottsdale, AZ (US); Rafael Nunez Nateras, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 28 days.

(21) Appl. No.: 14/359,846

(22) PCT Filed: Nov. 21, 2012

(86) PCT No.: PCT/US2012/066370
§ 371 (c)(1),
(2) Date: May 21, 2014

(87) PCT Pub. No.: WO2013/078393
PCT Pub. Date: May 30, 2013

(65) Prior Publication Data
US 2014/0315863 A1 Oct. 23, 2014

Related U.S. Application Data

(60) Provisional application No. 61/563,426, filed on Nov. 23, 2011.

(51) Int. Cl.
*G01N 33/574* (2006.01)
*A61K 39/07* (2006.01)
*A61K 39/00* (2006.01)

(52) U.S. Cl.
CPC ......... *G01N 33/57407* (2013.01); *A61K 39/07* (2013.01); *A61K 2039/585* (2013.01)

(58) Field of Classification Search
CPC .............................. G01N 33/574; A61K 39/07
USPC ........................................ 435/7.1; 424/246.1
See application file for complete search history.

(56) References Cited

PUBLICATIONS

Luo et al. (Cytokine, 2003, 21:17-26).*
Malmstrom et al. (European Urology, 2009, 56: 247-256).*
Chen et al. (PNAS, 2006, 103(45): 16894-16899).*
"Effect of BCG on Expression of T Cell-specific Transcription Factors T-bet and GATA-3 in Asthmatic Mice," Medical Science Articles, Jun. 9, 2011 [retreived on Jan. 9, 2012]. Retrieved from the Internet: <URL: http://www.medical-science.net/Respiratory-Disease/Effect-of-BCG-on-Expression-of-T-Cell-specific-Transcription-Factors-T-bet-and-GATA-3-in-Asthmatic-Mice.html>, 3 pages.
Agarwal et al., "Flow cytometric analysis of Th1 and Th2 cytokines in PBMCs as a parameter of immunological dysfunction in patients of superficial transitional cell carcinoma of bladder," *Cancer Immunol Immunother.*, 55(6):734-743, Epub Nov. 10, 2005.
Agarwal et al., "Serum Th1 and Th2 cytokine balance in patients of superficial transitional cell carcinoma of bladder pre- and post-intravesical combination immunotherapy," *Immunopharmacol Immunotoxicol.*, 32(2):348-356, Jun. 2010.
Chen et al., "Interaction of GATA-3/T-bet transcription factors regulates expression of sialyl Lewis X homing receptors on Th1/Th2 lymphocytes," *Proc Natl Acad Sci U S A.*, 103(45):16894-16899, Epub Oct. 30, 2006.
Choi et al., "Personal Factors Affecting Therapeutic Responses to BCG Vaccination in Asthmatics," *Allergy Asthma Immunol Res.*, 3(3):178-185, Epub May 18, 2011.
Fast Stats: An interactive tool for access to SEER cancer statistics. Surveillance Research Program, National Cancer Institute. http://seer.cancer.gov/faststats (Accessed on Feb. 24, 2011), 1 page.
Fleshner et al., "The National Cancer Data Base report on bladder carcinoma. The American College of Surgeons Commission on Cancer and the American Cancer Society," *Cancer*, 78(7):1505-1513, Oct. 1, 1996.
Griffiths et al., "Treatment of carcinoma in situ with intravesical bacillus Calmette-Guerin without maintenance," *J Urol.*, 167(6):2408-2412, Jun. 2002.
Hudson and Herr, "Carcinoma in situ of the bladder," *J Urol.*, 153(3 Pt 1):564-572, Mar. 1995.
Ketlinskiy and Simbirsev, "Cytokines: Structural and Functional Classification," *Cytokines*, Chpt. 1, p. 13, 2008.
Kudo et al., "[The role of lymphocytes and histiocytes as mechanism of action of BCG for bladder cancer]." *Nihon Hinyokika Gakkai Zasshi.*, 84(2):303-312, [Article in Japanese] Feb. 1993, [English Abstract].
Lamm, "Carcinoma in situ," *Urol Clin North Am.*, 19(3):499-508, Aug. 1992.
Lee et al., "Eosinophils in health and disease: the LIAR hypothesis," *Clin Exp Allergy.*, 40(4):563-575, Apr. 2010.
Luo and Knudson, "*Mycobacterium bovis* bacillus Calmette-Guérin-induced macrophage cytotoxicity against bladder cancer cells," *Clin Dev Immunol.*, vol. 2010, Article ID 357591. Epub Sep. 1, 2010.
Nadler et al., "Durability of the tumor-free response for intravesical bacillus Calmette-Guerin therapy," *J Urol.*, 152(2 Pt 1):367-373, Aug. 1994.
O'Donnell et al., "Role of IL-12 in the induction and potentiation of IFN-gamma in response to bacillus Calmette-Guérin," *J Immunol.*, 163(8):4246-4252, Oct. 15, 1999.
Ponticiello et al., "Analysis of local T lymphocyte subsets upon stimulation with intravesical BCG: a model to study tuberculosis immunity," *Respir Med.*, 98(6):509-514, Jun. 2004.
Protheroe et al., "A novel histologic scoring system to evaluate mucosal biopsies from patients with eosinophilic esophagitis," *Clin Gastroenterol Hepatol.*, 7(7):749-755.e11. Epub Apr. 1, 2009.

(Continued)

*Primary Examiner* — Yan Xiao
(74) *Attorney, Agent, or Firm* — Fish & Richardson P.C.

(57) ABSTRACT

This documents provided methods and materials involved in treating bladder cancer. This document also provides methods and materials involved in identifying bladder cancer patients likely or unlikely to respond to treatment (e.g., BCG therapy).

6 Claims, 7 Drawing Sheets

(56) References Cited

PUBLICATIONS

Ries et al., (eds). *SEER Cancer Statistics Review, 1975-2000*, National Cancer Institute. Bethesda, MD, http://seer.cancer.gov/csr/1975_2000/, 2003.

Samoszuk, "Eosinophils and human cancer," *Histol Histopathol.*, 12(3):807-812, Jul. 1997.

Schenkman and Lamm, "Superficial bladder cancer therapy," *ScientificWorldJournal.*, 4 Suppl 1:387-399, Jun. 28, 2004.

Simson et al., "Regulation of carcinogenesis by IL-5 and CCL11: a potential role for eosinophils in tumor immune surveillance," *J Immunol.*, 178(7):4222-4229, Apr. 1, 2007.

Sylvester et al., "Bacillus calmette-guerin versus chemotherapy for the intravesical treatment of patients with carcinoma in situ of the bladder: a meta-analysis of the published results of randomized clinical trials," *J Urol.*, 174(1):86-91; discussion 91-92, Jul. 2005.

Tatsumi et al., "Disease-associated bias in T helper type 1 (Th1)/Th2 CD4(+) T cell responses against MAGE-6 in HLA-DRB10401(+) patients with renal cell carcinoma or melanoma," *J Exp Med.*, 196(5):619-628, Sep. 2, 2002.

Wong et al., "Eosinophil ablation and tumor development," *Oral Oncol.*, 35(5):496-501, Sep. 1999.

Zuiverloon et al., "Markers predicting response to bacillus Calmette-Guérin immunotherapy in high-risk bladder cancer patients: a systematic review," *Eur Urol.*, 61(1):128-145, Epub Oct. 6, 2011.

International Search Report and Written Opinion for PCT/US2012/066370, mailed Mar. 14, 2013, 10 pages.

International Preliminary Report on Patentability for PCT/US2012/066370, issued May 27, 2014, 6 pages.

\* cited by examiner

TREATING BLADDER CANCER PATIENTS AND IDENTIFYING BLADDER CANCER PATIENTS RESPONSIVE TO TREATMENT

CROSS-REFERENCE TO RELATED APPLICATIONS

This application is a National Stage application under 35 U.S.C. 371 of International Application No. PCT/US2012/066370, having an International Filing Date of Nov. 21, 2012, which claims the benefit of U.S. Provisional Application Ser. No. 61/563,426, filed Nov. 23, 2011. The disclosure of the prior application is considered part of (and is incorporated by reference in) the disclosure of this application.

BACKGROUND

1. Technical Field

This document relates to methods and materials involved in treating bladder cancer patients. This document also relates to methods and materials involved in identifying bladder cancer patients likely or unlikely to respond to treatment (e.g., Bacillus Calmette-Guerin (BCG) therapy).

2. Background Information

Bladder cancer is a significant health problem in the United States, with an estimated 70,530 new cases diagnosed in 2010 and 14,680 estimated deaths. Bladder cancer currently ranks fourth in incidence among all cancers in males and eleventh among cancers in women. In recent decades, the overall incidence of bladder cancer appears to be rising, particularly among patients more than 55 years of age.

Transitional cell carcinoma, the most common pathologic subtype of bladder cancer, is observed in over 90% of tumors. The Tumor-Node-Metastases (TNM) classification (American Joint Committee on Cancer) is a commonly used and accepted staging system for bladder cancer. In this system, bladder cancer tumors have specifically defined characteristics. In particular, non-muscle invasive tumors, including papillary tumors confined to the epithelial mucosa, are termed Ta tumors. In contrast, tumors invading the subepithelial tissue (i.e., lamina propria) are defined as T1 tumors. Tumors with a distinct morphology and a dynamic phenotype are known as carcinoma in situ (Tis). Invasive tumors (T2-4a and T2-4b) are further defined and divided on the basis and extent of their invasive character following histopathologic evaluation.

SUMMARY

This document provides methods and materials involved in treating bladder cancer. This document also provides methods and materials involved in identifying bladder cancer patients likely or unlikely to respond to treatment (e.g., BCG therapy). For example, this document provides methods and materials involve in using the ratio of tumor-infiltrating Th2 lymphoid cells to tumor-infiltrating Th1 lymphoid cells to identify bladder cancer patients (e.g., Tis bladder cancer patients) who are likely to respond to an anti-cancer immunotherapy (e.g., BCG therapy). As described herein, patients having an initial bladder tissue biopsy with more tumor-infiltrating Th2 lymphoid cells than tumor-infiltrating Th1 lymphoid cells can be identified or classified as being likely to respond to BCG therapy, while patients having an initial bladder tissue biopsy that does not have more tumor-infiltrating Th2 lymphoid cells than tumor-infiltrating Th1 lymphoid cells can be identified or classified as being unlikely to respond to BCG therapy.

This document also provides methods and materials involve in using the level of eosinophil infiltration and/or degranulation to identify bladder cancer patients (e.g., Tis bladder cancer patients) who are likely or unlikely to respond to an anti-cancer immunotherapy (e.g., BCG therapy). As described herein, patients having an initial bladder tissue biopsy with elevated eosinophil infiltration and/or degranulation can be identified or classified as being likely to respond to BCG therapy, while patients having an initial bladder tissue biopsy that lacks elevated eosinophil infiltration and/or degranulation can be identified or classified as being unlikely to respond to BCG therapy. In some cases, both the ratio of tumor-infiltrating Th2 lymphoid cells to tumor-infiltrating Th1 lymphoid cells and the level of eosinophil infiltration and/or degranulation can be used in combination to identify bladder cancer patients (e.g., Tis bladder cancer patients) who are likely to respond to an anti-cancer immunotherapy (e.g., BCG therapy).

Having the ability to identify bladder cancer patients based, at least in part, on the ratio of tumor-infiltrating Th2 lymphoid cells to tumor-infiltrating Th1 lymphoid cells and/or the level of eosinophil infiltration and/or degranulation using a biopsy sample (e.g., an initial biopsy sample) can allow clinicians and patients to select appropriate treatment options with an increased degree of certainty.

In general, one aspect of this document features a method for assessing the likelihood of a bladder cancer patient to respond to an anti-cancer immunotherapy. The method comprises, or consists essentially of, determining whether or not the patient contains bladder cancer tissue with a ratio of tumor-infiltrating Th2 lymphoid cells to tumor-infiltrating Th1 lymphoid cells indicative of an increased likelihood of responding to the anti-cancer immunotherapy. The patient can be a human patient. The method can comprise determining whether or not a bladder tissue biopsy sample from the patient contains the bladder cancer tissue with the ratio. The ratio can be a ratio of GATA-3$^+$ to T-bet$^+$ tumor-infiltrating T cells. The method can comprise determining whether or not the patient contains bladder cancer tissue with a level of eosinophil infiltration or degranulation indicative of an increased likelihood of responding to the anti-cancer immunotherapy. The anti-cancer immunotherapy can be BCG therapy.

In another aspect, this document features a method for assessing the likelihood of a bladder cancer patient to respond to an anti-cancer immunotherapy. The method comprises, or consists essentially of, (a) determining whether or not the patient contains bladder cancer tissue with a ratio of tumor-infiltrating Th2 lymphoid cells to tumor-infiltrating Th1 lymphoid cells indicative of an increased likelihood of responding to the anti-cancer immunotherapy, (b) classifying the patient as being likely to respond to an anti-cancer immunotherapy if the patient contains the bladder cancer tissue with the ratio, and (c) classifying the patient as being unlikely to respond to an anti-cancer immunotherapy if the patient does not contain the bladder cancer tissue with the ratio. The patient can be a human patient. The method can comprise determining whether or not a bladder tissue biopsy sample from the patient contains the bladder cancer tissue with the ratio. The ratio can be a ratio of GATA-3$^+$ to T-bet$^+$ tumor-infiltrating T cells. The method can comprise determining whether or not the patient contains bladder cancer tissue with a level of eosinophil infiltration or degranulation indicative of an increased likelihood of responding to the anti-cancer immunotherapy. The anti-cancer immunotherapy can be BCG therapy.

In another aspect, this document features a method for assessing the likelihood of a bladder cancer patient to respond to an anti-cancer immunotherapy, wherein the method comprises, or consists essentially of, (a) detecting the presence of a ratio of bladder tumor-infiltrating Th2 lymphoid cells to bladder tumor-infiltrating Th1 lymphoid cells indicative of an increased likelihood of responding to the anti-cancer immunotherapy, and (b) classifying the patient as being likely to respond to the anti-cancer immunotherapy. The patient can be a human patient. The ratio can be a ratio of GATA-3$^+$ to T-bet$^+$ bladder tumor-infiltrating T cells. The method can comprise detecting the presence of a level of eosinophil infiltration or degranulation indicative of an increased likelihood of responding to the anti-cancer immunotherapy. The anti-cancer immunotherapy can be BCG therapy.

In another aspect, this document features a method for assessing the likelihood of a bladder cancer patient to respond to an anti-cancer immunotherapy. The method comprises, or consists essentially of, determining whether or not the patient contains bladder cancer tissue with a level of eosinophil infiltration or degranulation indicative of an increased likelihood of responding to the anti-cancer immunotherapy.

In another aspect, this document features a method for assessing the likelihood of a bladder cancer patient to respond to an anti-cancer immunotherapy. The method comprises, or consists essentially of, (a) determining whether or not the patient contains bladder cancer tissue with a level of eosinophil infiltration or degranulation indicative of an increased likelihood of responding to the anti-cancer immunotherapy, (b) classifying the patient as being likely to respond to an anti-cancer immunotherapy if the patient contains the bladder cancer tissue with the level, and (c) classifying the patient as being unlikely to respond to an anti-cancer immunotherapy if the patient does not contain the bladder cancer tissue with the level.

In another aspect, this document features a method for assessing the likelihood of a bladder cancer patient to respond to an anti-cancer immunotherapy. The method comprises, or consists essentially of, (a) detecting the presence of a level of eosinophil infiltration or degranulation indicative of an increased likelihood of responding to the anti-cancer immunotherapy, and (b) classifying the patient as being likely to respond to the anti-cancer immunotherapy.

In another aspect, this document features a method for treating bladder cancer. The method comprises, or consists essentially of, (a) detecting the presence, in bladder cancer tissue of a bladder cancer patient, of a ratio of tumor-infiltrating Th2 lymphoid cells to tumor-infiltrating Th1 lymphoid cells indicative of a decreased likelihood of responding to the anti-cancer immunotherapy, and (b) performing radical cystectomy procedure on the patient to treat the bladder cancer. The patient can be a human patient. The ratio can be a ratio of GATA-3$^+$ to T-bet$^+$ tumor-infiltrating T cells. The method can comprise detecting the presence, in bladder cancer tissue of a bladder cancer patient, of a level of eosinophil infiltration or degranulation indicative of a decreased likelihood of responding to the anti-cancer immunotherapy. The anti-cancer immunotherapy can be BCG therapy. The patient can receive the radical cystectomy procedure without having received a previous BCG therapy.

In another aspect, this document features a method for treating bladder cancer, The method comprises, or consists essentially of, (a) detecting the presence, in bladder cancer tissue of a bladder cancer patient, of a ratio of tumor-infiltrating Th2 lymphoid cells to tumor-infiltrating Th1 lymphoid cells indicative of a decreased likelihood of responding to the anti-cancer immunotherapy, and (b) administering intravesical mitomycin C or thiotepa chemotherapy to the patient to treat the bladder cancer. The patient can be a human patient. The ratio can be a ratio of GATA-3$^+$ to T-bet$^+$ tumor-infiltrating T cells. The method can comprise detecting the presence, in bladder cancer tissue of a bladder cancer patient, of a level of eosinophil infiltration or degranulation indicative of a decreased likelihood of responding to the anti-cancer immunotherapy. The anti-cancer immunotherapy can be BCG therapy. The intravesical mitomycin C or thiotepa chemotherapy can be administered to the patient before the patient receives BCG therapy.

In another aspect, this document features a method for treating bladder cancer. The method comprises, or consists essentially of, (a) detecting the presence, in bladder cancer tissue of a bladder cancer patient, of a level of eosinophil infiltration or degranulation indicative of a decreased likelihood of responding to the anti-cancer immunotherapy, and (b) performing radical cystectomy procedure on the patient to treat the bladder cancer. The patient can be a human patient. The ratio can be a ratio of GATA-3$^+$ to T-bet$^+$ tumor-infiltrating T cells. The method can comprise detecting the presence, in bladder cancer tissue of a bladder cancer patient, of a ratio of tumor-infiltrating Th2 lymphoid cells to tumor-infiltrating Th1 lymphoid cells indicative of a decreased likelihood of responding to the anti-cancer immunotherapy. The anti-cancer immunotherapy can be BCG therapy. The patient can receive the radical cystectomy procedure without having received a previous BCG therapy.

In another aspect, this document features a method for treating bladder cancer. The method comprises, or consists essentially of, (a) detecting the presence, in bladder cancer tissue of a bladder cancer patient, of a level of eosinophil infiltration or degranulation indicative of a decreased likelihood of responding to the anti-cancer immunotherapy, and (b) administering intravesical mitomycin C or thiotepa chemotherapy to the patient to treat the bladder cancer. The patient can be a human patient. The ratio can be a ratio of GATA-3$^+$ to T-bet$^+$ tumor-infiltrating T cells. The method can comprise detecting the presence, in bladder cancer tissue of a bladder cancer patient, of a ratio of tumor-infiltrating Th2 lymphoid cells to tumor-infiltrating Th1 lymphoid cells indicative of a decreased likelihood of responding to the anti-cancer immunotherapy. The anti-cancer immunotherapy can be BCG therapy. The intravesical mitomycin C or thiotepa chemotherapy can be administered to the patient before the patient receives BCG therapy.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
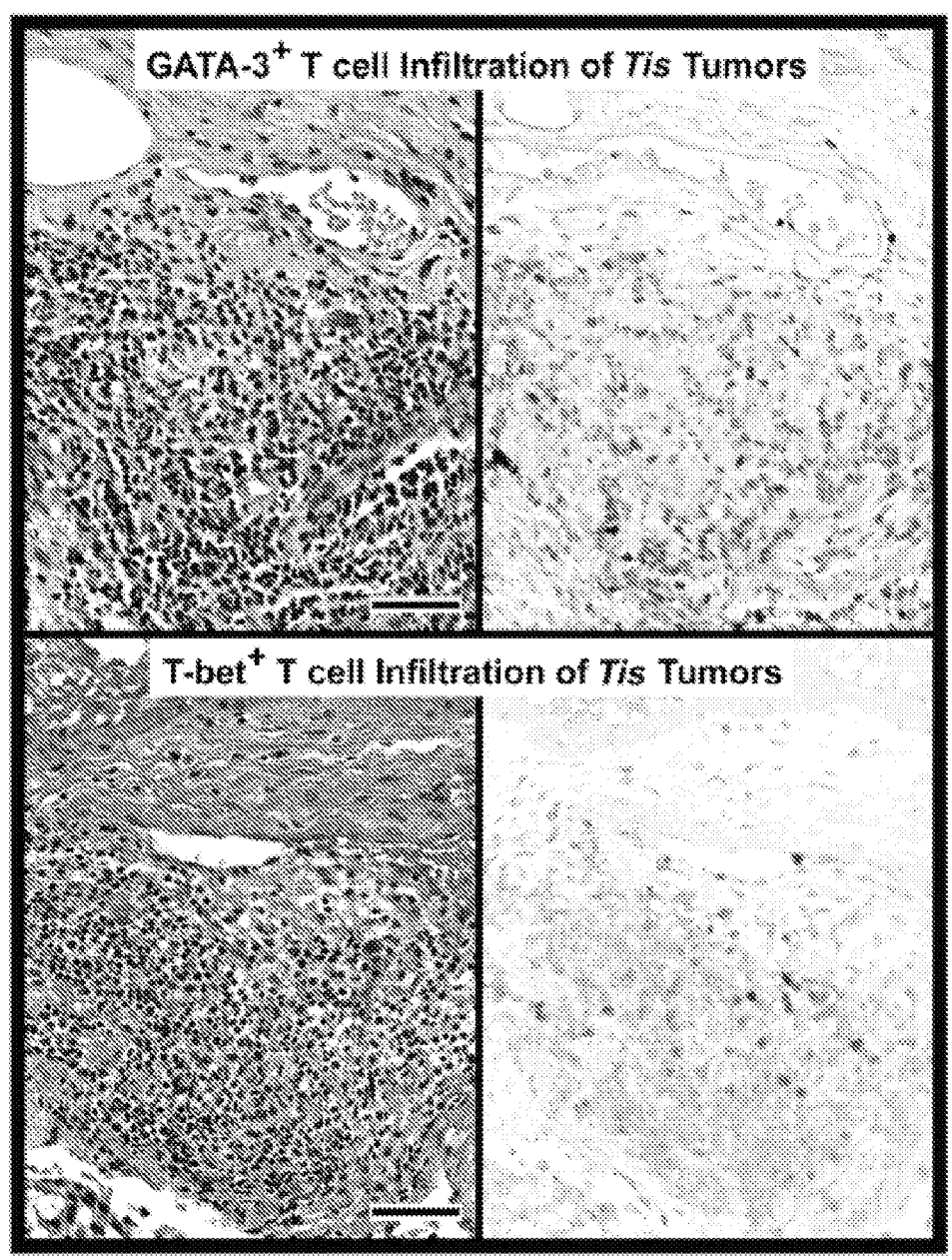
FIG. 1. T cell subtype-specific antibodies identify unique T cell populations infiltrating Tis bladder tumors Immunohistochemistry using antibodies specific for the master transcription factors, GATA-3 and T-bet, identify infiltrating Th2 polarized (brown staining cells) and Th1 polarized (red staining cells) lymphocytes, respectively. Scale bar=50 µm.

This document provides methods and materials involved in treating bladder cancer. This document also provides methods and materials involved in identifying bladder cancer patients likely or unlikely to respond to treatment (e.g., BCG therapy). For example, this document provides methods and materials for using the ratio of tumor-infiltrating Th2 lymphoid cells to tumor-infiltrating Th1 lymphoid cells to identify bladder cancer patients (e.g., Tis bladder cancer patients) who are likely to respond to an anti-cancer immunotherapy. Examples of anti-cancer immunotherapy include, without limitation, BCG therapy or α-interferon therapy. As described herein, patients having an initial bladder tissue biopsy with more tumor-infiltrating Th2 lymphoid cells than tumor-infiltrating Th1 lymphoid cells can be identified or classified as being likely to respond to BCG therapy. Patients having an initial bladder tissue biopsy that does not have more tumor-infiltrating Th2 lymphoid cells than tumor-infiltrating Th1 lymphoid cells can be identified or classified as being unlikely to respond to BCG therapy.

A ratio of tumor-infiltrating Th2 lymphoid cells to tumor-infiltrating Th1 lymphoid cells can be determined using any appropriate method of assessing the number of Th2 lymphoid cells and Th1 lymphoid cells present within a tissue sample (e.g., a tumor biopsy). For example, immunohistochemistry, immunofluorescence, or FACS® analyses techniques can be used to assess the level of tumor-infiltrating Th2 lymphoid cells and tumor-infiltrating Th1 lymphoid cells present within a tissue sample. When using immunohistochemistry techniques, antibodies to markers present on Th1 or Th2 lymphoid cells can be used. For example, antibodies such as anti-GATA-3 antibodies or anti-mouse/human GATA3 antibodies can be used to assess the number of Th2 lymphoid cells present within tissue, while antibodies such as anti-T-bet antibodies or anti-T-bet (e.g., H-210) antibodies can be used to assess the number of Th1 lymphoid cells present within tissue.

Once the numbers of tumor-infiltrating Th1 and Th2 lymphoid cells are determined, they can be compared to each other or used to determine the ratio of tumor-infiltrating Th2 lymphoid cells to tumor-infiltrating Th1 lymphoid cells. If the patient is determined to have an initial bladder tissue biopsy with more tumor-infiltrating Th2 lymphoid cells than tumor-infiltrating Th1 lymphoid cells, then that patient can be identified or classified as being likely to respond to BCG therapy. If the patient is determined to have an initial bladder tissue biopsy with less tumor-infiltrating Th2 lymphoid cells than tumor-infiltrating Th1 lymphoid cells, then that patient can be identified or classified as being unlikely to respond to BCG therapy. In some cases, patients having a bladder biopsy with a ratio of tumor-infiltrating Th2 lymphoid cells to tumor-infiltrating Th1 lymphoid cells that is greater than or equal to 3 or a cut-off ratio can be identified or classified as being likely to respond to BCG therapy, while patients having a bladder biopsy with a ratio of tumor-infiltrating Th2 lymphoid cells to tumor-infiltrating Th1 lymphoid cells that is less than or equal to 1.5 or a cut-off ratio can be identified or classified as being unlikely to respond to BCG therapy. In some cases, a cut-off ratio can be 1.5, 2.0, 2.5, or 3.0. It is to be understood that a ratio of tumor-infiltrating Th1 lymphoid cells to tumor-infiltrating Th2 lymphoid cells can be used in a similar manner as described herein regarding a ratio of tumor-infiltrating Th2 lymphoid cells to tumor-infiltrating Th1 lymphoid cells by making appropriate adjustments to the calculations.

Any appropriate sample can be used when measuring the levels of tumor-infiltrating Th1 and Th2 lymphoid cells. Such samples include, without limitation, tissue biopsies (e.g., bladder tissue biopsy) and tissue biopsy sections.

This document also provides methods and materials involve in using the level of eosinophil infiltration and/or degranulation to identify bladder cancer patients (e.g., Tis bladder cancer patients) who are likely to respond to an anti-cancer immunotherapy (e.g., BCG therapy). As described herein, patients having an initial bladder tissue biopsy with elevated eosinophil infiltration and/or degranulation can be identified or classified as being likely to respond to BCG therapy. Patients having an initial bladder tissue biopsy that lacks elevated eosinophil infiltration and/or degranulation can be identified or classified as being unlikely to respond to BCG therapy.

The level of eosinophil infiltration and/or degranulation present within a tissue sample (e.g., an initial bladder tissue biopsy) can be determined using any appropriate method. For example, immunohistochemistry, immunofluorescence, or FACS® analyses techniques can be used to assess the level of eosinophil infiltration and/or degranulation present within a tissue sample. When using immunohistochemistry techniques, antibodies to eosinophils or components of eosinophils can be used. For example, antibodies such as anti-human eosinophil peroxidase antibodies and anti-mouse eosinophil peroxidase antibodies can be used to assess the number of eosinophils or degranulating eosinophils present within tissue.

Once the numbers of eosinophils and/or degranulating eosinophils present within a tissue sample are determined, they can be compared to controls or used to calculate a score (e.g., an eosinophil activation index (EAI)). For example, an EAI can be calculated as described herein. In such cases, if the patient is determined to have an initial bladder tissue biopsy with an EAI greater than 4.0, 4.5, 5.0, or 5.5, then that patient can be identified or classified as being likely to respond to BCG therapy. If the patient is determined to have an initial bladder tissue biopsy with an EAI less than 5.5, 5.0, 4.5, or 4.0, then that patient can be identified or classified as being unlikely to respond to BCG therapy.

Any appropriate sample can be used when assessing eosinophils and/or degranulating eosinophils as described herein. Such samples include, without limitation, tissue biopsies (e.g., bladder tissue biopsy) and tissue biopsy sections.

In some cases, both the ratio of tumor-infiltrating Th2 lymphoid cells to tumor-infiltrating Th1 lymphoid cells and the level of eosinophil infiltration and/or degranulation can be used in combination to identify bladder cancer patients (e.g., Tis bladder cancer patients) who are likely to respond to an anti-cancer immunotherapy (e.g., BCG therapy). For example, the ratio of tumor-infiltrating Th2 lymphoid cells to tumor-infiltrating Th1 lymphoid cells can be multiplied or added to an EAI score to determine a Th2 biomarker signature that can be used to identify bladder cancer patients who are likely to respond to an anti-cancer immunotherapy (e.g., BCG therapy) as described herein.

This document also provides kits that can be used to determine the levels of tumor-infiltrating Th1 and Th2 lymphoid cells and/or the levels of eosinophils and/or degranulating eosinophils. Such a kit can contain anti-GATA-3 antibodies and anti-T-bet antibodies. In some cases, a kit containing anti-GATA-3 antibodies and anti-T-bet antibodies can include anti-eosinophil peroxidase antibodies (e.g., anti-human eosinophil peroxidase antibodies). In some cases, a kit provided herein can contain a reference chart that indicates a reference level or cut-off ratio for the levels of tumor-infiltrating Th1 and Th2 lymphoid cells and/or the levels of eosinophils and/or degranulating eosinophils that are indicative of patient likely or unlikely to respond to an anti-cancer immunotherapy (e.g., BCG therapy) as described herein.

This document also provides methods and materials for treating bladder cancer. For example, a bladder cancer patient can be assessed as described herein to determine whether the patient is likely or unlikely to respond to anti-cancer immunotherapy (e.g., BCG therapy). If the bladder cancer patient is identified as being likely to respond to anti-cancer immunotherapy (e.g., BCG therapy), then the patient can be administered an anti-cancer immunotherapy. For example, such a bladder cancer patient can be administered one or more (e.g., two, three, four, or more) rounds of BCG therapy. If the bladder cancer patient is identified as being unlikely to respond to anti-cancer immunotherapy (e.g., BCG therapy), then the patient can be administered an intravesical mitomycin C or thiotepa (N,N'N'-triethyl-enethiophosphoramide) chemotherapy, can be subjected to radical cystectomy, or both. For example, such a bladder cancer patient can be subjected to a radical cystectomy procedure to treat the bladder cancer. In some cases, a bladder cancer patient that is identified as being unlikely to respond to anti-cancer immunotherapy (e.g., BCG therapy) as described herein can be administered an intravesical mitomycin C or thiotepa chemotherapy, can be subjected to radical cystectomy, or both without having previously received an anti-cancer immunotherapy (e.g., BCG therapy) for the treatment of bladder cancer.

Figure 6:
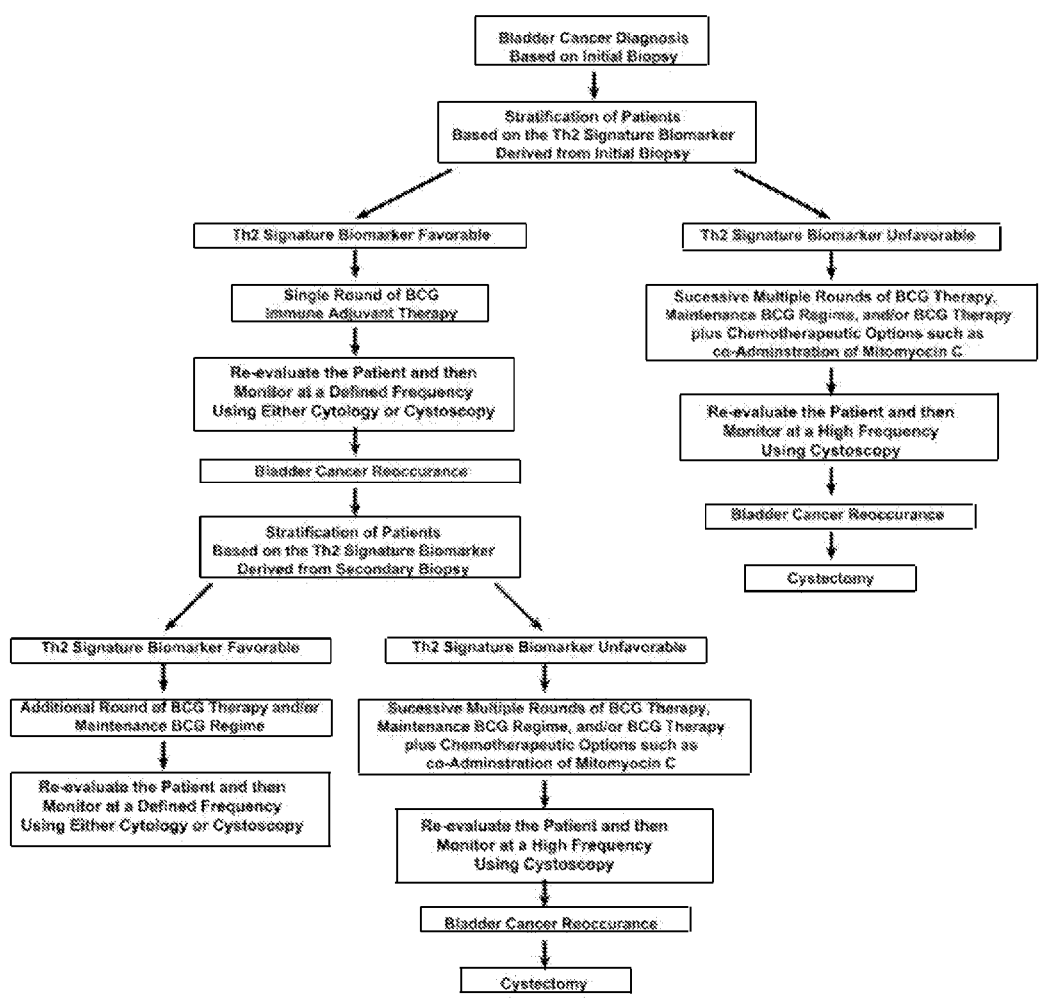
FIG. 6 is a flow chart plotting possible bladder cancer treatments for bladder cancer patients identified as being likely or unlikely to respond to anti-cancer immunotherapy (e.g., BCG therapy).
Figure 7:
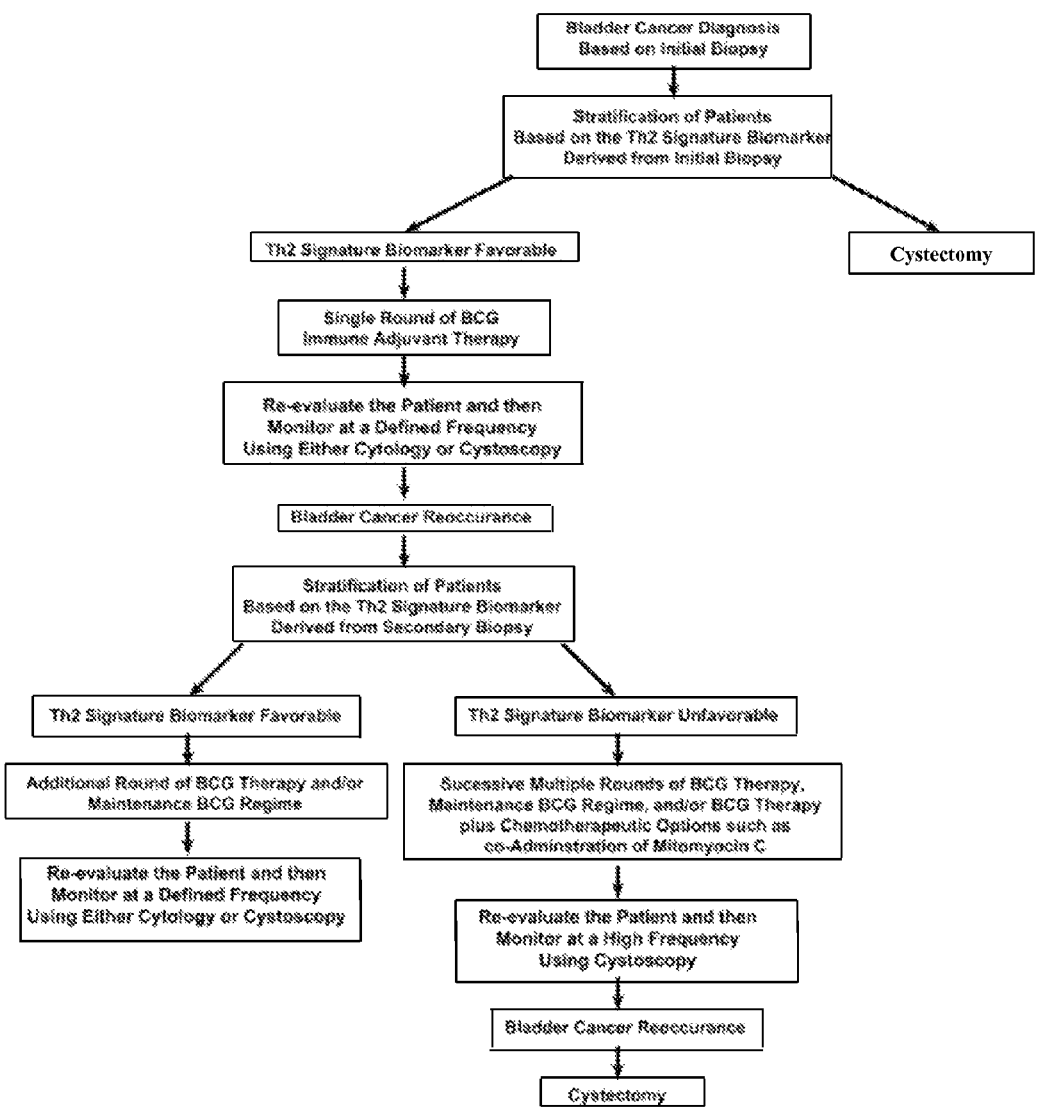
FIG. 7 is a flow chart plotting possible bladder cancer treatments for bladder cancer patients identified as being likely or unlikely to respond to anti-cancer immunotherapy (e.g., BCG therapy).

In some cases, a bladder cancer patient can be assessed and treated as set forth in FIG. 6 or FIG. 7.

The invention will be further described in the following examples, which do not limit the scope of the invention described in the claims.

EXAMPLES

Example 1

Assessing Bladder Cancer Outcomes

A study was performed using initial biopsies of bladder cancer patients from the urogenital service. Briefly, immunohistochemistry was performed using commercially available antibodies specific for Th2 (GATA-3$^+$; anti-human/mouse GATA3 (R&D Systems; Minneapolis, Minn.); and Th1 (T-bet$^+$ anti-T-bet (H-210): sc-21003 (Santa Cruz Biotechnology, Santa Cruz, Calif.)) lymphocytes and a monoclonal antibody specific for human/mouse eosinophil peroxidase (EPX-mAb). See, e.g., Protheroe et al., *Clin. Gastroenterol. Hepatol.*, 7:749-755 (2009).

Biopsies from three subgroups of patients were used: (i) ten normal control subjects (i.e., patients whose initial biopsies were pathology-negative for bladder cancer; (ii) ten Tis bladder cancer patients unresponsive to BCG immune therapy (i.e., BCG refractory (BCG$^-$)); and (iii) ten Tis bladder cancer patients who displayed no evidence of tumor follow BCG immune therapy (i.e., BCG responsive patients (BCG$^+$)).

Figure 2:
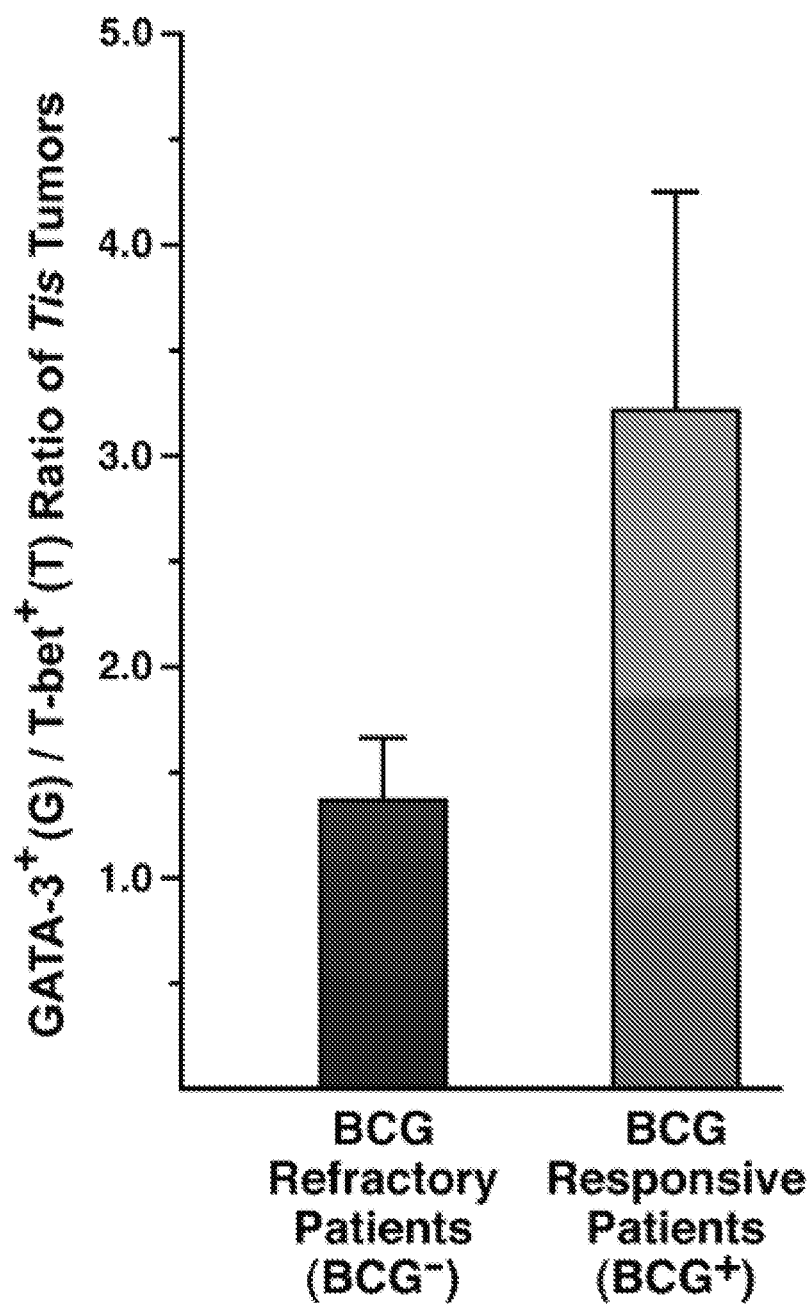
FIG. 2 is a graph plotting the relative number of bladder tumor infiltrating GATA-3$^+$ (G) vs. T-bet$^+$ (T) T cells (G/T ratio) at the time of initial biopsy/diagnosis. The G/T ratio differentiates Tis bladder cancer patients who are responsive from those who are un-responsive (refractory) to BCG immune therapy. G/T was scored for individual patient biopsies (n=9-10 per group) following immunohistochemical staining with antibodies specific for the respective transcription factors.

The following was performed to determine the ratio of GATA-3$^+$ tumor-infiltrating lymphoid cells to T-bet$^+$ tumor-infiltrating lymphoid cells (i.e., G/T ratio). Briefly, tumor-infiltrating T cells were systematically assessed in individual Tis patient biopsies by pathologists. Intra/inter-observer reliabilities were evaluated by blinded assessments of the slides by other investigators. Six serial sections of each biopsy were taken for evaluation. Sections 1 of 6 and 6 of 6 were used as isotype negative controls for the immunohistochemical staining of the biopsy. Section 3 of 6 was stained with Hematoxylin and Eosin (H&E) for evaluation to identify the maximal focus of the mononuclear proinflammatory infiltration. Sections 2 of 6 and 4 of 6 were subjected to immunostaining using antibodies specific for GATA-3$^+$ and T-bet$^+$ tumor-infiltrating T cells, respectively. Ten random high powered (400×) fields at the maximum focus of mononuclear infiltration were examined, and the numbers of GATA-3$^+$ (G) and T-bet$^+$ (T) tumor-infiltrating T cells were enumerated to define a G/T ratio for each patient sample. Representative photomicrographs of staining for each T cell-specific antibody are shown in FIG. 1. Evaluations of these sections revealed that it was possible to stratify bladder cancer patients on the basis of G/T ratio generating two subgroups, patients with a highly Th2 polarized immune microenvironment (G/T≥3) and patients with a Th1 polarized subgroup with a G/T ratio≤1.5. More significantly, correlation of these scores with subsequent patient outcomes following BCG immune therapy demonstrated that patient responsiveness to BCG treatment (i.e., tumor elimination) trended with the higher G/T ratio patients (FIG. 2).

Figure 3:
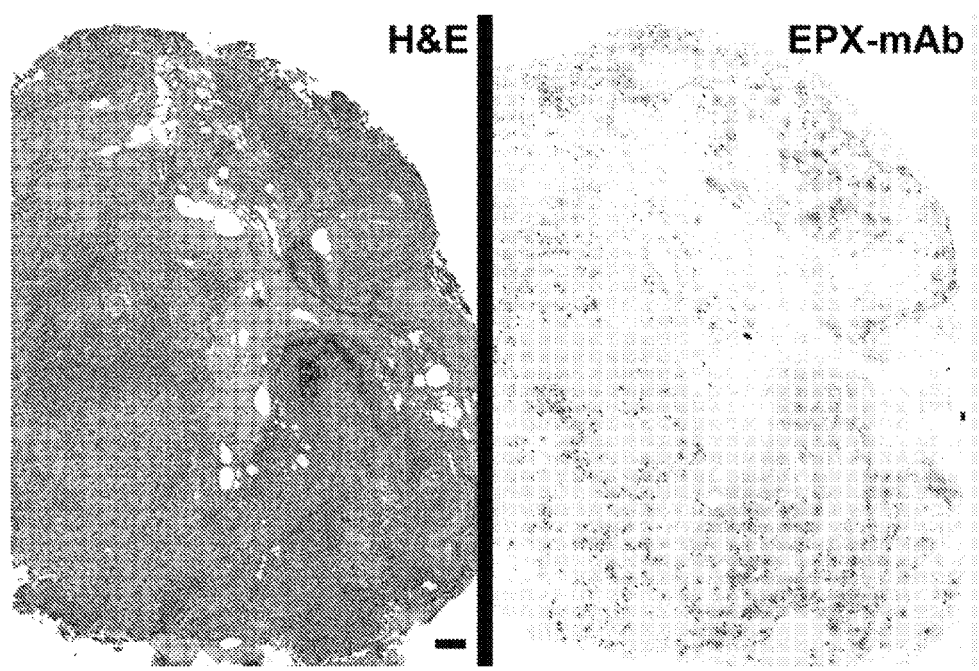
FIG. 3 contains photographs of Tis bladder tumors stained with H&E or an eosinophil peroxidase-specific monoclonal antibody (EPX-mAb). Significant levels of eosinophil infiltration accompanied by activation (i.e., eosinophil degranulation) were observed Immunohistochemistry using EPX-mAb demonstrates a robust tissue eosinophilia in Tis bladder tumors (red staining cells) that is often accompanied by eosinophil activation leading to areas of eosinophil peroxidase release/deposition (i.e., red staining areas of extracellular matrix). Scale bar=100 µm.
Figure 4:
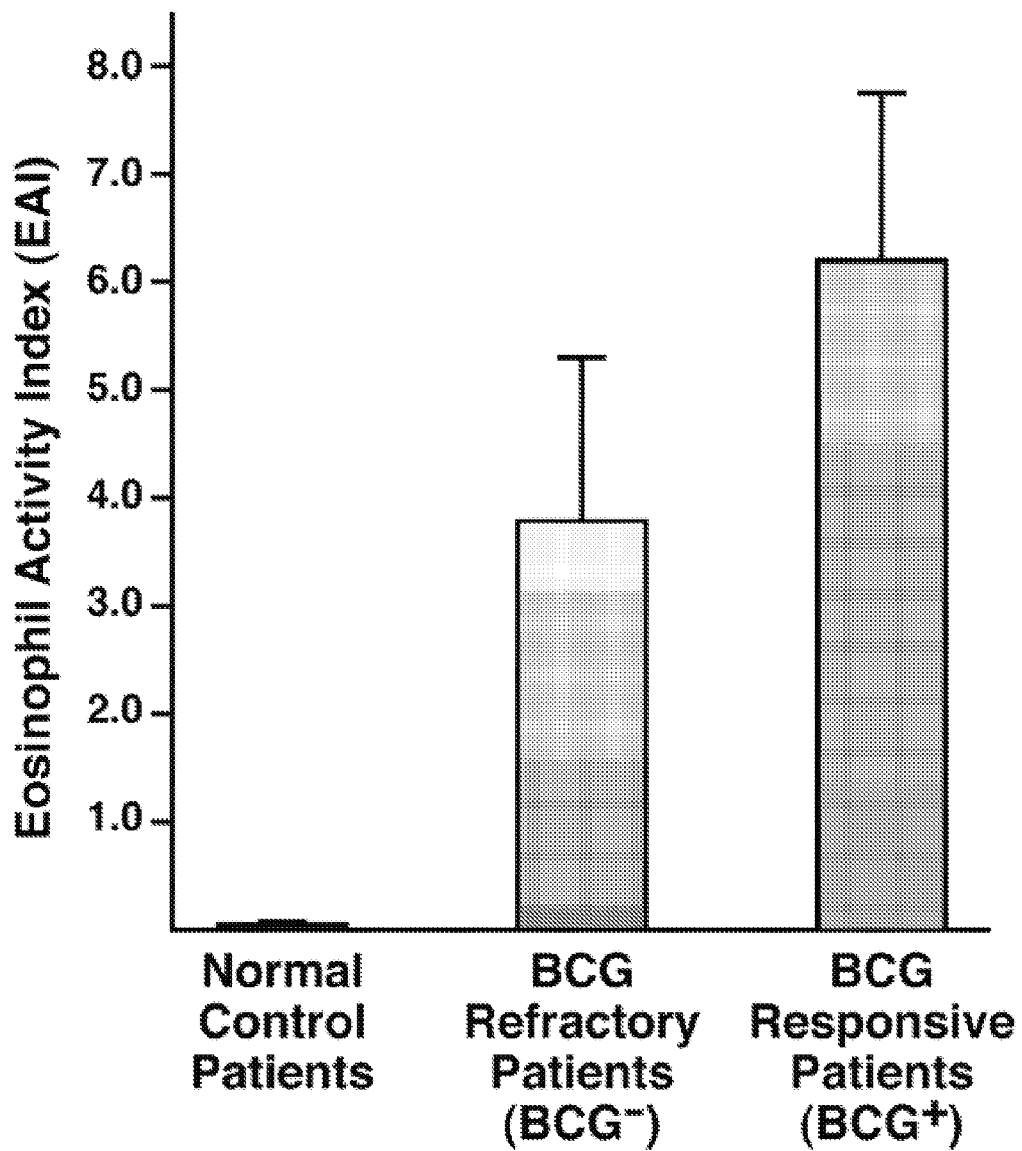
FIG. 4 is a graph plotting an the number of eosinophils or degranulating eosinophils present within tissue (EAI) for biopsies obtained at the time of initial diagnosis from Tis bladder cancer patients who were responsive or un-responsive (refractory) to BCG immune therapy. Biopsies from normal patients were used as a control. The EAI differentiated patients who are responsive from those who are un-responsive (refractory) to BCG immune therapy. EAI was scored for individual patient biopsies (n=9-10 per group) following immunohistochemical staining with the EPX-mAb.

EPX-mAb based immunohistochemistry was used to evaluate eosinophil infiltration of the bladder cancer patient biopsies as well as to quantify the level of degranulation observed in each biopsy (biopsy section 5 of 6). Representative examples of this EPX-mAb-based immunostaining are shown in FIG. 3. These evaluations led to the development of an eosinophil activation index (EAI) expressed as the product of a numerical score of eosinophil tissue infiltration (0=no eosinophils/40X hpf; 1=1-4 eosinophils/40X hpf; 2=5-10 eosinophils/40X hpf; and 3=>10 eosinophils/40X hpf) and a numerical score assessing eosinophil degranulation (1=no evidence of degranulation; 2=degranulation in <20% of the biopsy; 3=degranulation evident in 20-50% of the biopsy; and 4=degranulation evident in >50% of the biopsy). Eosinophil infiltration and degranulation were unique to bladder cancer with no evidence of either event in control (i.e., non-cancerous) bladder tissue. In addition, the initial biopsies of BCG responsive patients (BCG$^+$) displayed a higher EAI relative to BCG refractory patients (BCG$^-$) (FIG. 4).

Figure 5:
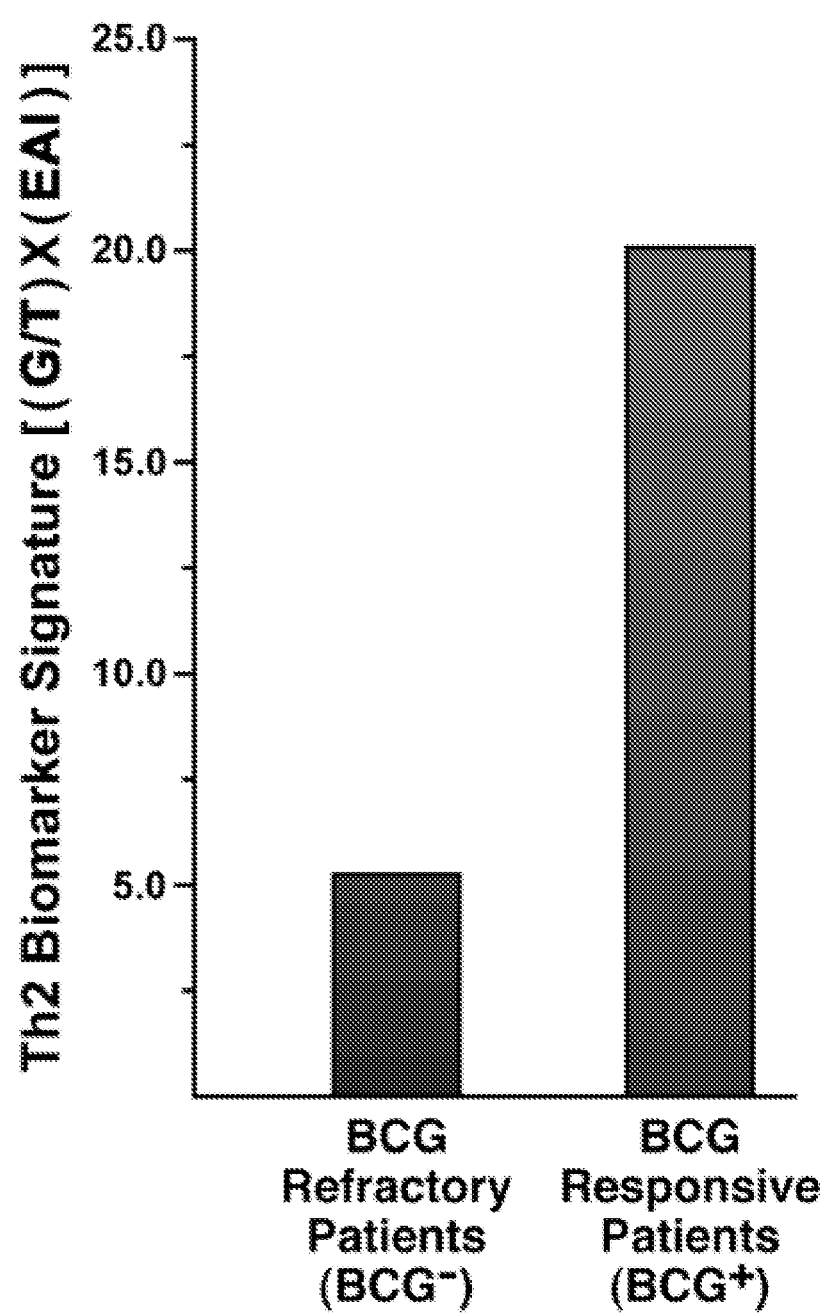
FIG. 5 is a graph plotting a Th2 biomarker signature for Tis bladder tumors from patients who were responsive or un-responsive (refractory) to BCG immune therapy. The Th2 biomarker signature represents a robust metric or score that stratifies bladder cancer patients into subgroups either responsive or refractory to BCG immune therapy. The numerical product of the signature derived from evaluations of the G/T ratio and EAI of a given bladder tumor (i.e., Th2 biomarker signature score) provided a quantifiable measure that was predictive of patient outcome following BCG immune therapy.

The product of the G/T ratio and the EAI score from each patient (i.e., G/T ratio*EAI score resulted in a Th2 biomarker signature that easily stratified subjects into BCG responsiveness and unresponsive subgroups (FIG. 5).

These results demonstrate that G/T ratios, eosinophil infiltration and/or degranulation, or both G/T ratios and eosinophil infiltration and/or degranulation can be used to assess bladder cancer biopsies (e.g., initial Tis bladder tumor biopsies) to determine whether or not the patient will be responsiveness to BCG immune therapy.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating bladder cancer, wherein said method comprises:
    (a) detecting the presence, in bladder cancer tissue of a bladder cancer patient not previously receiving BCG therapy to treat said bladder cancer, of a ratio of tumor-infiltrating Th2 lymphoid cells to tumor-infiltrating Th1 lymphoid cells indicative of a decreased likelihood of responding to an anti-cancer immunotherapy, and
    (b) administering, to treat said bladder cancer, intravesical mitomycin C or thiotepa chemotherapy to said patient who did not previously receive BCG therapy to treat said bladder cancer.

2. The method of claim 1, wherein said patient is a human patient.

3. The method of claim 1, wherein said ratio is a ratio of GATA-3$^+$ to T-bet$^+$ tumor-infiltrating T cells.

4. The method of claim 1, wherein said method comprises detecting the presence, in bladder cancer tissue of a bladder cancer patient, of a level of eosinophil infiltration or degranulation indicative of a decreased likelihood of responding to said anti-cancer immunotherapy.

5. The method of claim 1, wherein said anti-cancer immunotherapy is BCG therapy.

6. The method of claim 1, wherein said intravesical mitomycin C or thiotepa chemotherapy is administered to said patient before said patient receives BCG therapy.

* * * * *